United States Patent [19]

Palinczar

[11] Patent Number: 4,731,242

[45] Date of Patent: Mar. 15, 1988

[54] WATERPROOF SUNSCREEN COMPOSITIONS

[76] Inventor: Victor Palinczar, 435 Adeline St., Trenton, N.J. 08611

[21] Appl. No.: 842,559

[22] Filed: Mar. 21, 1986

[51] Int. Cl.$^4$ ............................ A61K 7/42; A61K 7/44
[52] U.S. Cl. .......................................... 424/59; 424/60
[58] Field of Search ...................................... 424/59, 60

[56] References Cited

U.S. PATENT DOCUMENTS

| | | | |
|---|---|---|---|
| 3,011,950 | 12/1961 | Mehaffey | 424/59 |
| 3,330,731 | 7/1967 | Mehaffey | 424/47 |
| 3,445,566 | 5/1969 | Skoultchi et al. | 424/47 |
| 3,472,940 | 10/1969 | Osipow | 424/59 X |
| 3,529,055 | 9/1970 | Skoultchi et al. | 424/59 X |
| 3,670,073 | 6/1972 | Shepherd et al. | 424/47 |
| 3,755,560 | 8/1973 | Dickert et al. | 424/59 |
| 3,895,104 | 7/1975 | Karg | 424/47 |

Primary Examiner—Dale R. Ore

[57] ABSTRACT

An effective, aesthetic water-proof sunscreen composition which provides ultraviolet light protection to the skin includes monohydric alcohols in an amount from 15% up to about 90% by weight, from about 1% to about 30% by weight of an active sunscreen agent, from about 0.1% to about 40.0% by weight of polyamide polymer and from about 0.1% to about 5% by weight of an acrylic acid crosslinked polymer, and from about 0.1% to about 8.0% by weight of an alkaline neutralizing agent.

The composition may optionally contain up to about 15% by weight of hydroxyl donors; up to about 20% by weight of water-insoluble emollients; up to about 20% by weight of suspended particulate matter; and up to about 3% by weight of fragrance oil.

21 Claims, No Drawings

WATERPROOF SUNSCREEN COMPOSITIONS

BACKGROUND OF THE INVENTION

1. Field of the Invention

This invention relates to novel sunscreen compositions which, when applied to the human skin provides protection against the harmful effects caused by ultraviolet radiation. More particularly, this invention relates to sunscreen compositions in the form of viscous liquids and gels wherein an ultraviolet light-absorbing ingredient is placed on the skin and is provided with increased water resistant characterisics with the aid of polymeric binder. Most particularly, this invention relates to sunscreen compositions that are water proof and fulfill the guidelines established by the Food and Drug Administration, as listed in the Federal Register: Volume 43, Number 166.

2. Discussion of the Relevant Art

Sunscreen compositions are commonly used during outdoor activity. Many people have occupations which require them to be exposed to the sun for long periods of time. Others choose to use their free time in outdoor recreations e.g. sunbathing, playing golf, surfing, fishing, skiing and swimming. All of these activities promote perspiration or allow the body to come in contact with water. Numerous sunscreen compositions have been developed which absorb ultraviolet light in a region of 280 to 320 nanometers (2800–3200 Angstroms; referred to as the "erythemal region") to protect the human body against this radiation that produces erythema and skin cancer, whether the source be from the sun or from man made devices. These compositions also incorporate ultraviolet absorbing agents that absorb in the region between 320 and 380 nanometers (3200–3800 Angstroms) and should be resistant to removal from the skin by perspiration or water in order to broaden and prolong their effectiveness.

Numerous substantive sunscreen agents, and substantive and water-resistant sunscreen compositions are available today. Development of substantive sunscreen agents and sunscreen compositions containing these substantive agents are illustrated in U.S. Pat. No. 3,864,473 issued to Cicendelli; U.S. Pat. No. 4,004,074 issued to Gerecht; and U.S. Pat. No. 4,256,664 issued to Epstein. These compositions make use of sunscreen agents that are not approved by the FDA and their topical use is limited.

No known sunscreen agent, that achieves a degree of water-resistancy, has been approved by the Food and Drug Administration. FDA approved sunscreen agents have, however, been incorporated into compositions which upon application to the skin physically keep the sunscreen agent on the skin during perspiration or immersion in water. The majority of these compositions make use of polymeric materials that are either emulsified in the composition or carried to the skin by a vehicle in which a continuous polymeric film is cast on the skin.

The use of an acid form of a cross-linked co-polymer of ethylene-maleic anhydride composition in the form of a gel is illustrated in U.S. Pat. No. 3,821,363 issued to Black. The use of acrylate/acrylic acid co-polymer compositions in the form of oils and emulsions are illustrated in U.S. Pat. No. 4,172,122 issued to Kubik. In U.S. Pat. No. 4,254,102 issued to Kaplan there is described the use of compositions containing hydroxyethylcellulose in conjunction with a surface active agent and a fatty alcohol. In U.S. Pat. No. 4,193,989 issued to Eng, there is described gel compositions of hydroxypropyl cellulose acetate as the film former.

Known compositions that make use of polymers to form a continuous polymeric film in which the active sunscreen agent is homogeneously dispersed throughout the matrix of the film have numerous disadvantages. Aqueous based compositions in which the polymer is usually emulsified have long drying rates on the skin, foam on the skin during application and during the drying cycle leave the skin feeling tacky. These compositions, if not fully dried, also have a tendency to allow particulate matter, such as beach sand, to adhere to the skin. Furthermore, the water-resistant properties of these aqueous based compositions are decreased if they are not fully dried before perspiration or entry into water. The formation of a continuous protective film on the skin is prevented by compositions which make use of solvent systems because they cannot tolerate large amounts of oil and other emollients. Without the use of emollients in compositions containing alcohols, the skin may become dry and irritated. Generally these compositions are also formulated in thin solutions with low viscosities which make them difficult to apply to the skin in an even manner.

Compositions, which make use of a polyamide resin as the film former, in combination with ethanol as a solvent and are effective in resisting water wash off, are illustrated in U.S. Pat. No. 3,895,104 issued to Karg. These compositions, however, are low in viscosity, and are difficult to apply to the skin evenly thus permitting spot burning to occur, which may result in extreme pain and blistering of the skin. This effect is more pronounced with individuals having fair complexions and who normally use sunscreen products having high SPF (Sun Protection Factor) values. Water-resistant compositions described heretofore or that are currently being marketed in addition to being difficult to apply to the skin evenly, lack the ability to be made in a range of viscosities, thus limiting the formulator in his selection of ingredients to be used in a composition and separate systems must be developed to fulfill the needs of the consumer. Furthermore, compositions having high solvent concentrations lack the ability to homogeneously suspend particulate matter throughout the matrix of the composition thereby preventing the use of insoluble solid ingredients which have a tendency to prevent ultraviolet radiation from being absorbed by the skin.

The present invention overcomes the shortcomings of known water-resistant sunscreen compositions by incorporating ingredients which resist removal of the active sunscreen agent and particulate suspended matter that reflect and/or absorb ultraviolet radiation by perspiration and water when applied to the skin. The present invention, in combination with ingredients that, allow the composition to be pseudo-plastic with a range of viscosities, have the ability to suspend insoluble particulate matter, allows the composition to be applied to the skin evenly and easily to all parts of the body and protects the skin from the harmful effects of the sun's radiation. There is a need for such a product for both health and cosmetic reasons. Ingredients may be available which exhibit one or more of these desired attributes. However, the combination of these attributes for use in preparing water-proof sunscreen systems has not been demonstrated. Ingredients that have not been used previous to this invention in water-proof sunscreen compositions for fulfilling these requirements are the combination of active sunscreen agents, polyamide polymers, monohydric alcohols, acrylic acid crosslinked polymers, and alkaline neutralizing agents.

SUMMARY OF INVENTION

This invention relates to very effective, highly aesthetic water-proof sunscreen compositions in the form of viscous liquids and gels which provide ultraviolet light protection to the skin comprising monohydric alcohols in an amount of up to about 90% by weight from about 1% to about 30% by weight of an active sunscreen agent, from about 0.1% to about 40.0% by weight of polyamide polymer, from about 0.1% to about 5% by weight of an acrylic acid cross-linked polymer, and from about 0.1% to 8.0% by weight of an alkaline neutralizing agent.

The compositions may optionally contain up to about 15% by weight of hydroxyl donors, up to about 20% by weight of water-insoluble emollients, up to about 20% by weight of suspended particulate matter, and up to about 3% by weight of fragrance oil.

DESCRIPTION OF THE PREFERRED EMBODIMENTS

It has been discovered that highly effective, non-irritating, cosmetically aesthetic water-proof sunscreen compositions in the form of viscous liquids and gels containing monohydric alcohols, such as, ethanol or isopropanol, a polymeric film former, such as polyamide polymer, active sunscreen agent, an acrylic acid cross-linked polymer and an alkaline neutralizing agent are prepared by solubilizing the polyamide polymer in the monohydric alcohol, and then adding the active sunscreen agent. Upon complete dissolution of the sunscreen agent, the acrylic acid cross-linked polymer is dispersed in the solution until the mixture is free of any agglomerates. The alkaline neutralizing agent may be added to the mixture separately, however, it is preferably added in the form of a solution of the monohydric alcohol used in the composition. The degree of viscosity of the composition is adjusted by varying the amounts of the acrylic acid cross-linked polymer and the neutralizing agent in stoichiometric proportions. Upon complete neutralization of the acrylic acid cross-linked polymer, the composition is then placed in the desired container and is ready for use by a consumer.

It has also been discovered that the composition may contain water for the purpose of allowing acrylic acid crosslinked polymer and the alkaline neutralizing agent to react to a fuller extent increasing the viscosity and clarity of the composition.

It has further been discovered that the composition may additionally contain water-insoluble emollients which serve to prevent the skin from drying and leaving the skin feeling smooth and soft. The water-insoluble emollients also add body to the composition as it is applied to the skin and decrease tackiness of the composition during dryout. It has still further been discovered that the composition may contain suspended particulate matter which serve as an auxiliary means to reflect and/or filter ultraviolet radiation. The suspended particulate matter may also serve as a cosmetic additive to make the composition more glamorous in the container and on the skin.

It has additionally been discovered that the polyamide polymer, although having a propensity for oxygenated organic compounds, has a good tolerance with non-polar compounds when used in conjunction with a monohydric alcohol. This compatibility allows for a broad range in the overall solubility parameter of the composition. Such a range in the solubility parameter allows the composition to contain high levels of non-polar ingredients such as diisopropyl adipate, polyoxypropylene (14) butyl ether and menthy phenyl polysiloxanes.

It has still further been discovered that the neutralized acrylic acid cross-linked polymer produces thixotropic lotions and gels which allow suspension of the particulate matter while spreading easily on the skin when shear is applied.

It has still additionally been discovered that when a water-insoluble neutralizing agent is combined with the acrylic acid cross-linked polymer the resulting end product of this combination is also water-insoluble.

In addition to these ingredients the composition may additionally contain fragrance oil. These ingredients are more specifically described below.

While applicant does not wish to be limited by any theory of the mechanism of the activity of the invention, it is believed that the use of polyamide polymer in combination with the neutralized acrylic acid cross-linked polymer is very important in maintaining both the degree of water resistance and the ability to be compatible with a variety of ingredients to form a continuous film on the skin of the compositions mentioned herein.

When the water-proof composition is applied on the skin the application feels cool and soothing. The monohydric alcohol which is usually a major constituent of the composition evaporates from the skin leaving a water-insoluble flexible film consisting of a high ratio of active sunscreen agents to organic and inert ingredients. The water-insoluble film also helps prevent the loss of the active sunscreen agents by physical abrasion and is uneffected by bodily salts expelled from the body during perspiration. It is believed that the polyamide/neutralized acrylic acid cross-linked polymer film allows perspiration to pass through the continuous film in the vapor state, thereby leaving the film intact and continuous. It is further believed that the film, in addition to containing the active sunscreen agent at a high ratio of sunscreen agent to polyamide/neutralized acrylic acid cross-linked polymer, prevents the migration of the active sunscreen agent from the matrix of the film, keeping the active sunscreen agent on the surface of the skin, thereby decreasing percutaneous absorption through the skin of the active sunscreen agent. It is therefore believed that the combination of these actions cause these compositions to be effective for long periods of time and to resist removal by water and perspiration.

MONOHYDRIC ALCOHOLS

Monohydric alcohols, such as ethanol isopropanol are the preferred alcohols used in this invention. The present invention may contain up to 90% of monohydric alcohols. The preferred amount of the monohydric alcohol is from about 25% to about 85% and most preferably from about 35% to about 75%. Amounts of less than 25% are also acceptable if used in combination with ingredients that allow the polyamide resin polymer to remain in solution.

It will be understood that if one replaces any portion of the monohydric alcohol, with one ingredient or a mixture of ingredients that do not have rates of evaporation and viscosity similar to that of the monohydric alcohol, composition prepared with these ingredients or a mixture of these ingredients, will have their drying rates, water-resistancy sun protection factor, and overall cosmetic aesthetics reduced. It will be further understood that the monohydric alcohols provide excellent compatibility with an array of cosmetically acceptable ingredients, and any ingredient combination may be made without departing from this spirit and scope of this invention.

THE POLYMERIC FILM-FORMER

Any polyamide polymer, which is insoluble in water, non-irritating, non-toxic and is compatible with a carrier material and an active sunscreen agent and which when applied to the skin forms a continuous, impervious, water-resistant film in which the active sunscreen agent is homogeneously dispersed, can be used.

Polymeric material useful herein includes homopolymers and copolymers of acrylamide. The pendant amide moiety may have substituted groups attached to the nitrogen atoms wherein said substituted groups may be selected from the groups consisting of hydrogen, alkyl, substituted alkyl, alkenyl, aryl, substituted aryl and alkaryl groups. The groups on each nitrogen atom present in the polyacrylamide may have the same or dissimilar substitution. As to the alkyl groups they are preferably $C_1$ to $C_{10}$ such as methyl, ethyl, n-propyl, butyl, amyl, hexyl, heptyl, nonyl groups and the like; the alkenyl groups can be allyl, methallyl, crotyl and the like; and the substituted alkyls are exemplified by the cyano, hydroxy, alkoxy or halo $C_1$–$C_{10}$ radicals with examples being cyanoethyl, cyano-n-propyl, cyano-n-butyl, hydroxyethyl, hydroxyisopropyl, hydroxyhexyl, methoxymethyl, methoxypropyl, propoxypropyl, butyoxyethyl, chloropropyl, chloroethyl, chlorodecyl and the like. With respect to the aryl radicals these can be phenyl, tolyl, xylyl, diphenyl and the like; the substituted aryl radicals are illustrated by anisyl, hydroxyethyl phenyl, meta-chlorotolyl and the like; and the alkaryl groups can be benzyl, phenethyl, phenol n-propyl, 2,4-dimethylbenzyl and the like. The polymeric material contemplated herein does not of necessity have to have all substituted groups the same. Therefore, the polymer contemplated may contain nitrogen atoms of the pendant amide groups which are unsubstituted, monosubstituted or disubstituted and are all the same or, alternatively, pendant groups which differ one from another such as where some pendant groups are unsubstituted amide groups and some are substituted amides. The resulting polymeric material must be insoluble in water, be capable of forming a substantive film and be soluble in alcohols.

Polymeric materials useful herein include homopolymers and copolymers of acrylamide such as polyacrylamide, N,N-dimethylacrylamide, N,N-diethylacrylamide, N,N-dibutylacrylamide, N,N-di(B-hydroxyethyl)acrylamide, N,N-dimethoxymethylacrylamide, N-methoxymethyl acrylamide, N-ethyl-N-cyanoethyl acrylamide, N-phenyl acrylamide, (N,N-dimethyl) (N'N'-diethyl)acrylamide, (N,N-dimethyl) (N'ethyl) acrylamide, (N,N-diphenyl) (N'-methyl) acrylamide and the like.

Polyacrylamides useful in this invention may be made in any of the known methods such as by free radical polymerization of the desired monomeric constituents.

Polyamide useful in forming the long lasting sunscreen composition of this invention may be polymers formed from the raction of polyamines with a polybasic acid. Methods of preparing these polyamides by condensation of polyamines and polycarboxylic acids or anhydrides are well known in the art and need not be described here. The polyamides may be derived from such polyamines as ethylenediamine, diethylene-triamine, triethylenetetramine, tetraethylenepentamine, propylenediamine, 1,4-diaminobutane, 1,3-diaminobutane, hexamethylenediamine, 3,3-iminobispropylamine and the like. Typical polycarboxylic acids which may be condensed with the polyamines to form the desired polyamide are oxalic, malonic, succinic, glutaric, adipic, palmitic, suberic, azelaic, sebacic, malic, phthalic, cyclohexandicarboxylic, and the like as well as their isomers, homologs and andydrides. Alternately, or in addition to the above polycarboxylic acids, the polyamide may be formed from unsaturated polycarboxylic acids or anhydrides such as maleic, fumaric, citraconic and itaconic acids and the like.

The present invention may contain from about 0.1% to about 40% by weight of these polyamide polymers or a mixture thereof. The preferred amount of polyamide polymer is from about 0.5% to about 25% by weight of the total composition. The chemical composition of polyamide polymers, is highly complex and usually contain a broad spectrum of molecular weight species. For this reason applicant wishes not to be limited to the polyamide polymers mentioned in the present invention.

THE ACTIVE SUNSCREEN AGENT

Any active sunscreen agent, capable of absorbing the harmful effects of ultraviolet radiation which, in non-irritating, non-toxic and is compatible with the ingredients used in the composition and which when applied to the skin are homogeneously dispersed throughout the film formed by the polyamide resin polymer, can be used. Active sunscreen agents that met these criteria are: PABA (para-aminobenzoic acid); Cinoxate (2-ethoxyethyl p-methoxycinnamate); diethanolamine p-methoxycinnamate; digalloyl trioleate; Dioxybenzone (2,2'-dihydroxy-4-methoxybenzophenone); ethyl 4-[bis(hydroxypropyl)]- aminobenzoate; 2-ethylhexyl 2-cyano-3,3-diphenylacrylate; ethylhexyl p-methoxycinnamate; 2-ethylhexyl salicylate; glyceryl aminobenzoate; Homosalate (3,3,5-trimethylcyclohexyl salicylate); Menthyl Anthranilate (menthyl o-aminobenzoate); Oxybenzone (2-hydroxy-4-methoxybenzophenone); Padimate A (amyl p-dimethylaminobenzoate); 2-phenylbenzimidazole-5-sulfonic acid; Sulisonbenzone (5-benzoyl-4-hydroxy-2-methoxybenzenesulfonic acid); triethanolamine salicylate; 4-Tert. butyl-4-methoxydibenzoylmethane; and benzalphthalide.

The present invention may contain from about 1% to about 30% by weight of these active sunscreen agents or a mixture thereof. The preferred total amount of the active sunscreen agent is dependent upon the SPF value (sun protection factor) desired to be obtained. The preferred sunscreen agents in the present invention are Padimate O in amounts from 2% to about 10% by weight; Padimate A in amounts from 1% to about 8% by weight; 2-ethylhexyl salicylate in amounts from 3% to about 8% by weight; ethylhexyl p-Methoxycinnamate in amounts from 2% to about 8% by weight; Dioxybenzone from 1% to about 5% by weight and Oxybenzone from 1% to about 7% by weight.

THE ACRYLIC ACID CROSSLINKED POLYMER

Acrylic acid polymers, such as CARBOPOLS manufactured by (B.F. GOODRICH CO., CLEVELAND, OHIO) are crosslinked polymers of acrylic acid having an average equivalent weight from about 72 to about 80; an average molecular weight from about 400,000 to about 5,000,000; a specific gravity from about 1.30 to about 1.50; and are represented by the chemical formula $(CH_2CHCOOH)_n$. The acrylic acid polymer in combination with the proper neutralizing agent providdes an adequate method for increasing the viscosity of the composition while producing a lubricating effect on the skin. Furthermore the acrylic acid polymer produces compositions that are pseudo-plastic and thixotropic in nature having high yield values. The high yield value allows particulate matter to be suspended for extremely long periods of time. Examples of suitable acrylic acid polymers are those sold under the trade name CARBOPOL (907, 910, 941, 934, and 940).

The chemical composition of polymers is highly complex and usually contain a broad spectrum of molecular weight species. For this reason applicant wishes not to be limited only to the polymers mentioned in the present invention.

The preferred acrylic acid polymers are CARBOPOL (941, 935 and 940) which have average molecular weights ranging from about 1,000,000 to about 5,000 000. The present composition may contain from about 0.1% to about 5% of the acrylic acid polymers. The preferred amount of acrylic acid polymer is from 0.4% to about 2.5%.

ALKALINE NEUTRALIZING AGENT

Any alkaline, soluble in alcohol, capable of neutralizing the acrylic acid crosslinked polymer sufficient enough to uncoil the acrylic acid molecule by allowing the formation of hydrogen bonds, which is non-irritating non-toxic and is compatible with the ingredients used in the composition which when applied to the skin allows the formation of a continuous polymer film in which the active sunscreen agent is homogeneously dispersed, can be used. Alkaline neutralizing agents that meet these criteria are amines selected from a group of amines consisting of, but not limited to di(2-ethylhexyl)amine; amines derived from fatty acids such as cocamine, dimethyl lauramine, and dimethyl hydrogenated tallow amine and poly(ethylene glycol) amines derived from fatty acids such as polyoxyethylene (15) coconut amine, polyoxyethylene (2) oleamine and polyoxyethylene (10) stearamine.

The preferred amines of the present invention are di(2-ethylhexyl)amine; cocamine and polyoxyethylene (15) coconut amine. The present composition may contain from about 0.1% to about 8% by weight of amines. The preferred amount of amine is from 0.4% to about 2.5% by weight.

HYDROXYL DONOR

The present composition may also contain, as an optional ingredient from about 0% to about 15% by weight of a hydroxyl donor. Hydroxyl donors which can be used in the present invention, are ingredients which contain high levels of hydroxyl groups in their molecule and form strong hydrogen bonds with the acrylic acid crosslinked polymer, which are selected from a group consisting of polyhydroxy and polyethoxy compounds such as diols, triols and polyols and water. Unless the use of water in the composition causes incompatibility, it is the most preferred hydroxyl donor. The optional use of the hydroxyl donor allows the formation of strong hydrogen bonds with the acrylic acid crosslinked polymer which in its presolvated state is tightly coiled and its thickening capabilities limited. The hydroxyl donor allows the acrylic acid crosslinked polymer to uncoil and form laminated networks of polymer molecules producing an increase in the viscosity of the composition.

In addition to increasing viscosity, the hydroxyl donor has the ability to improve the clarity of the product if this is a desired feature of the composition. From a cosmetic standpoint many users of sunscreen products have a strong preference for transparent compositions. In addition to properties the hydroxyl donor also allow the composition to spread on the skin more evenly and decrease the rate of evaporation of the monohydric alcohol. The preferred amount of hydroxyl donor is from about 2% to about 10% by weight.

THE SUSPENDED PARTICULATE MATTER

The present composition may additionally contain, as an optional ingredient, from about 0% to about 20% by weight of suspended particulate solid matter which are insoluble in both the monohydric alcohols and hydroxyl donor. From these solids a group of solids have been selected which are inert in the composition, having a low degree of irritation and toxicity, that are generally considered safe for topical use that provide for a cosmetic benefit and reflects and/or absorbs ultraviolet radiation. Solids that are used for cosmetic purposes are solid materials that produce a "glitter", "sparkle", or "pearlesant" effect when exposed to natural or artificial light. Preferred solid for cosmetic purposes include such solids as, bismuth oxychloride, mica and colorized acrylic polyester as manufactured by (MEADOW-BROOK INVENTIONS, INC., BERNARDSVILLE, N.J.) under the name of "CRYSTALINA." The preferred solid in the present composition, for cosmetic use, is the colorized acrylic polyester. The preferred amount of solid used for cosmetic purposes in the present invention is from 0.5% to about 10% by weight.

The preferred solids used in the present invention for the purpose of reflecting or absorbing ultraviolet radiation are solids such as zinc oxide, or titanium dioxide. These solids are generally used in a powder form in which the average particle size is less than 100 microns. The preferred amount of suspended particulate solid matter used in the present invention for the purpose of reflecting ultraviolet radiation is from about 5% to about 15% by weight.

THE WATER-INSOLUBLE EMOLLIENT

The present composition may additionally contain, as an optional ingredient, from about 0% to about 20% by weight of water-insoluble materials are usually in the liquid state at room temperature (about 22 degrees C.) and have a water solubility of less than about 1% at 25 degrees C. From these liquids a group of liquids have been selected which are organic in nature having a low degree of irritation and toxicity, that are generally considered safe for topical use, that provide a softening or soothing effect on surface skin tissue are hereinafter referred to as the water-insoluble liquid emollients in the present composition. Preferred water-insoluble liquid emollients include fatty acids such as oleic and recinoleic; fatty alcohols such as oleyl, lauryl, and hexadecyl (ENJAY); esters such as diisopropyl adipate, benzoic acid esters of $C_9$-$C_{15}$ alcohols, and iso-nonyl iso-nonanoate; alkanes such as mineral oil; alkenes such as polybutenes; silicones such as methyl phenyl polysiloxane and ethers such as polyoxypropylene butyl ethers and polyoxypropylene cetyl ethers. The most preferred water-insoluble liquid emollients are: methyl phenyl polysiloxane and polyoxypropylene (14) butyl ether. The preferred amount of water-insoluble liquid emollient is from about 2% to about 15% by weight, preferably from about 4% to about 10%.

The water-insoluble liquid emollient can be used to control the rate of evaporation of the monohydric alcohol. In addition to providing emolliency, they also aid in controlling the amount of product deposited on the skin and the rigidity of the continuous polymer film. One skilled in the art will easily be able to adjust the cosmetic aesthetics and physical characteristics of the composition by combining various suitable water-insoluble emollients in the proper proportions with the ingredients of the composition mentioned hereintofore.

The water sunscreen compositions of the present invention may be made in a variety of ways to those skilled in the art. In one procedure, the monohydric alcohol and the polyamide polymer are heated to a temperature of about 60 degrees C. in a suitable vessel with agitation. When dissolution is complete, the active sunscreen agent is added and mixed until a complete solution is formed. The acrylic acid crosslinked polymer is then added slowly to the mixture until a homogeneous dispersion is formed free of agglemerate. A solution of the alkaline neutralizing and monohydric alcohol is then added to this mixture. The mixture is allowed to cool and mixed again to ensure uniform neutralization of the acrylic acid crosslinked polymer. The optional ingredients may then be added. If the composition is to contain suspended particulate solid matter, gentle mixing is preferred to avoid grinding, which may have an effect on the composition's viscosity. The composition may then be filled in a suitable container for consumer use.

Another procedure for preparing water-proof sunscreen composition of the present invention would be to dissolve the polyamide polymer, the active sunscreen agent and the neutralizing agent in a portion of the monohydric alcohol in a suitable vessel with agitation. When solution is complete the suspended particulate solid matter is then added to the mix with sufficient agitation to keep the solid particle from settling. At this time the hydroxyl donor is added. The remaining portion of the monohydric alcohol and the desired amount of acrylic acid crosslinked polymer is mixed with agitation in a separate vessel until a smooth and complete dispersion is formed. The monohydric alcohol/acrylic acid dispersion is then added to the vessel containing the mixture of monohydric alcohol, polyamide polymer, active sunscreen agent, alkaline neutralizing agent, suspended particulate solid matter and the hydroxyl donor. The latter mixture is stirred during the combining of the two phases. Upon completing the combination, the composition is additionally mixed until a homogeneous mixture is obtained. The finished product may then be placed in a suitable container for consumer use.

The following formulation examples are given to further illustrate the present invention. It is to be understood, however, that the invention is not limited hereto.

The formulation examples were applied on the skin and allowed to dry for fifteen minutes. They were then tested using the prescribed water resistancy test method described in the Federal Register Volume 43, number 166, and were considered to be resistant to removal from the skin by water and perspiration while maintaining their dry SPF value for periods of up to 80 minutes.

EXAMPLE 1

| INGREDIENTS | PERCENT BY WEIGHT |
| --- | --- |
| Ethanol | 75.0 |
| Poly N,N—Dimethyl Acrylamide | 10.0 |
| Water | 5.0 |
| Padimate O | 8.0 |
| *Carbopol 940 | 1.0 |
| Di(2-Ethylhexyl)amine | 1.0 |
| | 100.0 |

*Carbopol 940 is the trade name for Acrylic Acid crosslinked polymer marketed by B.F. Goodrich, Cleveland, Ohio.

EXAMPLE 2

| INGREDIENTS | PERCENT BY WEIGHT |
| --- | --- |
| Ethanol | 74.0 |
| *Polytrap FLM 203 | 12.0 |
| Water | 5.0 |
| Ethylhexyl P—Methoxycinnamate | 7.0 |
| Carbopol 940 | 1.0 |
| Di(2-Ethylhexyl)amine | 1.0 |
| | 100.0 |

*Polytrap FLM 203 is the trade name for an ethanolic solution of a polyacrylamide polymer marketed by Wickhen, Inc., Huguenot, New York.

EXAMPLE 3

| INGREDIENTS | PERCENT BY WEIGHT |
| --- | --- |
| Ethanol | 54.0 |
| Polytrap FLM 203 | 12.0 |
| Padimate O | 8.0 |
| Ethylhexyl p-methoxycinnamate | 7.0 |
| Padimate A | 5.0 |
| Carbopol 940 | 1.5 |
| Di(2-ethylhexyl)amine | 1.5 |
| Glitter-aluminized acrylic polyester | 2.0 |
| Polyoxypropylene (14) butyl ether | 3.0 |
| Water | 6.0 |
| | 100.0 |

EXAMPLE 4

| INGREDIENTS | PERCENT BY WEIGHT |
| --- | --- |
| Isopropanol | 10.00 |
| Ethanol | 52.00 |
| Polytrap FLM 203 | 12.00 |
| Oxybenzone | 3.00 |
| Padimate O | 8.00 |
| Methyl phenyl polysiloxane | 3.00 |
| Diisopropyl adipate | 3.00 |
| Carbopol 940 | 1.25 |
| Di(2-ethylhexyl)amine | 1.25 |
| Water | 6.50 |
| | 100.00 |

EXAMPLE 5

| INGREDIENTS | PERCENT BY WEIGHT |
| --- | --- |
| Ethanol | 56.50 |
| Padimate O | 8.00 |
| Ethyl 4-[bis(hydroxypropyl)] aminobenzoate | 5.00 |
| Zinc oxide | 10.00 |
| Carbopol 940 | 1.25 |
| Di(2-ethylhexyl)amine | 1.25 |
| Polytrap FLM 203 | 12.00 |
| Water | 6.00 |
| | 100.00 |

What I claim is:

1. A water-proof sunscreen composition comprising:
  A. from about 15% to about 90% by weight of a monohydric alcohol;
  B. from about 0.1% to about 40% by weight of a water-insoluble polyamide polymer;
  C. from about 1.0% to about 30% by weight of an active ultraviolet radiation absorber;
  wherein the improvement comprises:
  D. from about 0.1% to about 5.0% by weight of an acrylic acid crosslinked polymer having a molecular weight from about 400,000 to about 5,000,000; an average equivalent weight from about 72 to about 80 and a specific gravity from about 1.30 to about 1.50 and represented by the formula $(CH_2CHCOOH)_n'$; and
  E. from about 0.1% to about 5.0% by weight of an alkaline neutralizing agent.

2. A water-proof sunscreen composition according to claim 1 wherein said ultraviolet radiation absorber is selected from the group consisting of para-aminobenzoic acid; 2-ethoxyethyl p-methoxycinnamate; diethanolamine-p-methoxycinnamate; digalloyl trioleate; 2,2'-dihydroxy-4-methoxybenzophenone; ethyl 4-(bis[hydroxypropyl])aminobenzoate; 2-ethylhexyl salicylate; glyceryl aminobenzoate; 3,3,5-trimethylcyclohexyl salicylate; 2-ethylhexyl 2-cyano-3,3-diphenylacrylate; ethylhexyl p-methoxycinnamate; menthyl o-aminobenzoate; 2-hydroxy-4-methoxybenzophenone; amyl p-dimethylaminobenzoate; octyl p-dimethylaminobenzoate; 2-phenylbenzimidazole-5-sulfonic acid; 5-benzoyl-4-hydroxy-2 methoxybenzene sulfonic acid; triethanolamine salicylate; 4-tert. butyl-4-methoxy-dibenzoylmethane; and benzalphthalide.

3. A water-proof sunscreen composition according to claim 1 where said alkaline neutralizing agent is selected from the group consisting of di(2-ethyl-hexyl)amine, amines derived from fatty acids and poly)ethylene glycol) amines derived from fatty acids.

4. A water-proof sunscreen composition according to claim 1 which additionally comprises:
  A. from about 0% to about 15% by weight of a hydroxyl donor which is water;
  B. from about 0% to about 20% by weight of a water-insoluble liquid, organic emollient compound having a water-solubility of less than 1% at 25 degrees C. selected from the group consisting of fatty alcohols, fatty acids, esters; ethers, alkanes, alkenes, and polysiloxanes;
  C. from about 0% to about 20% by weight of suspended particulate solid matter; and
  D. from about 0% to about 3% by weight of a fragrance oil.

5. A water-proof sunscreen composition according to claim 4 wherein:
  A. said monohydric alcohol is ethanol, isopropanol and benzyl alcohol;
  B. said active ultraviolet radiation absorber is selected from the group consisting of para-aminobenzoic acid; 2-ethoxyethyl p-methoxycinnamate; diethanolamine-p-methoxycinnamate; digalloyl trioleate; 2,2'-dihydroxy-4-methoxybenzophenone; ethyl 4-(bis[hydroxypropyl])-aminobenzoate; 2-ethylhexyl salicylate; glyceryl aminobenzoate; 2-ethylhexyl 2-cyano-3,3-diphenylacrylate; ethylhexyl p-methoxycinnamate; 3,3,5-trimethylcyclohexyl salicylate; menthyl o-aminobenzoate); 2-hydroxy-4-methoxybenzophenone; amyl p-dimethylaminobenzoate; octyl p-dimethylaminobenzoate; 2-phenylbenzimidazole-5-sulfonic acid; 5-benzoyl-4-hydroxy-2 methoxybenzene sulfonic acid; triethanolamine salicylate; 4-tert. butyl-4-methoxy-dibenzoylmethane; and benzalphthalide.
  C. said alkaline neutralizing agent is selected from the group consisting of di(2-ethylhexyl)amine, amines derive from fatty acids and poly(ethylene glycol) amines derived from fatty acids;
  D. said suspended particulate solid matter is selected from the group consisting of aluminumized acrylic polyester, and metallic oxides; and
  E. said liquid emollient is selected from the group consisting of oleic acid, lauryl alcohol, diisopropyl adipate, mineral oil, polybutene, phenyl methyl polysiloxane, and polyoxypropylene butyl ether.

6. A water-proof sunscreen composition having an active ultraviolet radiation absorber comprising:
  A. from about 0.5.% to about 25% by weight of a polyamide polymer which is the condensation product of at least one polycarboxylic acid and at least one polyamine having a solubility in water of less than 1% at 25 degrees C. and a solubility in monohydric alcohols greater than 5% at 25 degrees C.;
  B. from about 25% to about 85% by weight of a monohydric alcohol selected from the group consisting of ethanol and isopropanol;
  C. from about 2% to about 20% by weight of an active ultraviolet radiation absorber selected from the group consisting of para-aminobenzoic acid; 2-ethoxyethyl p-methoxycinnamate; diethanolamine p-methoxycinnamate; digalloyl trioleate; 2,2'-dihydroxy-4-methoxybenzophenone; ethyl 4-(bis[hydroxypropyl])-aminobenzoate; 2-ethylhexyl salicylate; glyceryl aminobenzoate; 2-ethylhexyl 2-cyano-3,3 -diphenylacrylate; ethylhexyl p-methoxycinnamate; 3,3,5-trimethylcyclohexyl salicylate; menthyl o-aminobenzoate; 2-hydroxy-4-methoxybenzophenone; amyl p-dimethylaminobenzoate; octyl p-dimethylaminobenzoate; 2-phenylbenzimidazole-5-sulfonic acid; 5-benzoyl-4-hydroxy-2 methoxybenzene sulfonic acid; triethanolamine salicylate; 4-tert.-butyl-4-methoxy-dibenzoylmethane; and benzalphtalide;
  D. from about 2% to about 10% by weight of a hydroxyl donor which is water;
  E. from about 0.5% to about 15% by weight of suspended particulate solid matter selected from the group consisting of aluminumized acrylic polyester and metallic oxides;
  F. from about 2% to about 15% by weight of a water-insoluble liquid emollient selected from the group consisting of oleic acid, lauryl alcohol, diisopropyl adipate, mineral oil, polybutene, phenyl methyl polysiloxane and polyoxypropylene butyl ether wherein the improvement comprises:

G. from about 0.4% to about 2.5% by weight of an acrylic acid crosslinked polymer having an average molecular weight from about 1,000,000 to about 4,000,000; and H. from about 0.4% to about 2.5% by weight of an alkaline neutralizing agent selected from a group consisting of di(2-ethylhexyl)amine, amines derived from fatty acids and poly(ethylene glycol)amines derived from fatty acids.

7. A water-proof sunscreen composition according to claim 6 wherein the monohydric alcohol comprises ethanol.

8. A water-proof sunscreen composition according to claim 6 wherein the active ultraviolet radiation absorber comprises Padimate.

9. A water-proof sunscreen composition according to claim 6 wherein the active ultraviolet radiation absorber comprises Dioxybenzone.

10. A water-proof sunscreen composition according to claim 6 wherein the active ultraviolet radiation absorber comprises Oxybenzone.

11. A water-proof sunscreen composition according to claim 6 wherein the active ultraviolet radiation absorber comprises ethyl 4-bis(hydroxypropyl)-aminobenzoate.

12. A water-proof sunscreen composition according to claim 6 wherein the active ultraviolet radiation absorber comprises ethyl p-methoxycinnamate.

13. A water-proof sunscreen composition according to claim 6 wherein the active ultraviolet radiation absorber comprises Padimate O and Dioxybenzone.

14. A water-proof sunscreen composition according to claim 6 wherein the polyamide polymer is a polyacrylamide.

15. A water-proof sunscreen composition according to claim 6 wherein the acrylic acid crosslinked polymer has a molecular weight from about 3,500,000 to about 4,500,000.

16. A water-proof sunscreen composition according to claim 6 wherein the alkaline neutralizing agent comprises di(2-ethylhexyl) amine.

17. A water-proof sunscreen composition according to claim 6 wherein the suspended particulate matter comprises colorized acrylic polyester.

18. A water-proof sunscreen composition according to claim 6 wherein the suspended particulate matter comprises zinc oxide.

19. A water-proof sunscreen composition according to claim 6 wherein the suspended particulate matter comprises titanium dioxide.

20. A water-proof sunscreen composition according to claim 6 wherein the water insoluble liquid emollient comprises polyoxypropylene (14) butyl ether.

21. A water-proof sunscreen composition according to claim 6 wherein the water insoluble liquid emollient comprises phenyl dimethyl polysiloxane.

* * * * *